(12) United States Patent
Navari et al.

(10) Patent No.: US 8,637,265 B2
(45) Date of Patent: Jan. 28, 2014

(54) CATHEPSIN E AS A MARKER OF COLON CANCER

(75) Inventors: Rudolph M. Navari, Granger, IN (US); Mary Prorok, South Bend, IN (US); Francis J. Castellino, Granger, IN (US)

(73) Assignee: University of Notre Dame, Notre Dame, IN (US)

( * ) Notice: Subject to any disclaimer, the term of this patent is extended or adjusted under 35 U.S.C. 154(b) by 0 days.

(21) Appl. No.: 12/979,889

(22) Filed: Dec. 28, 2010

(65) Prior Publication Data

US 2012/0225425 A1 Sep. 6, 2012

Related U.S. Application Data

(62) Division of application No. 11/312,780, filed on Dec. 21, 2005, now Pat. No. 7,892,750.

(60) Provisional application No. 60/638,240, filed on Dec. 23, 2004.

(51) Int. Cl.
*G01N 33/574* (2006.01)

(52) U.S. Cl.
USPC .......................................... 435/7.23

(58) Field of Classification Search
None
See application file for complete search history.

(56) References Cited

U.S. PATENT DOCUMENTS 6,709,832 B1 * 3/2004 Von Knebel Doeberitz et al. ............................ 435/7.23

OTHER PUBLICATIONS

Wong et al (Eur. J. Histo., 47(2):143-150, 2003).*
Campbell (Monoclonal Antibody Technology, Laboratory Techniques in Biochemistry and Molecular Biology, Elsevier Science Publishers B.V.: Amsterdam, The Netherlands, vol. 13, pp. 1-32, 1984).*

* cited by examiner

*Primary Examiner* — Brad Duffy
(74) *Attorney, Agent, or Firm* — Thompson Coburn LLP; Denise L. Mayfield

(57) ABSTRACT

Elevated levels of cathepsin E (catE) are demonstrated to be diagnostic of intestinal forms of cancer, such as colorectal cancer. Elevated levels of cathepsin E (catE, monomeric forms) are demonstrated to be detectable in the urine of animals having colorectal cancer, and a diagnostic/screening method for identifying and/or detecting colorectal cancer in an animal from a urine sample is provided. Specific tissue immunohistochemcial staining for catE (monomeric forms) in dysplastic tissue is also disclosed, and is shown to correlate with the level of dysplastic lesion severity. Hence, a method for identifying and determining the level of dysplastic lesion severity is provided. Cathepsin E mRNA transcription and expression levels are also demonstrated to be upregulated in dysplastic tissue, relative to non-dysplastic tissue. Hence, a method for transcriptionally profiling an animal to monitor the progression of colorectal disease is provided.

9 Claims, 4 Drawing Sheets

CATHEPSIN E AS A MARKER OF COLON CANCER

CROSS-REFERENCE TO RELATED APPLICATIONS

This application claims priority to U.S. Provisional App. No. 60/638,240, entitled "Cathepsin E as a Marker of Colon Cancer," filed Dec. 23, 2004, and to U.S. application Ser. No. 11/312,780, filed Dec. 21, 2005, now patented as U.S. Pat. No. 7,892,750. The present application is a divisional application of U.S. application Ser. No. 11/312,780. The entire disclosure and contents of the above applications are hereby incorporated by reference herein.

EFS INCORPORATION PARAGRAPH

Sequence Listing

The instant application contains a Sequence Listing which has been submitted in ASCII format via EFS-Web and is hereby incorporated by reference in its entirety. Said ASCII copy, created on May 24, 2012, is named 34341455.txt and is 1,747 bytes in size.

GOVERNMENT INTEREST STATEMENT

The United States Government has rights in this invention pursuant to federal funding provided in United States Department of Defense Contract No. DAMD17-03-1-0206.

BACKGROUND

1. Field of the Invention

The present invention relates generally to methods of detecting colon cancer, and more particularly, to a method for detecting colon cancer using a marker, cathepsin E.

2. Related Art

The identification of molecular markers and proteomic patterns in the inception and progression of colon cancer is a major goal in the management of this disease. In the search for sensitive and accurate markers of colon cancer, $APC^{Min/+}$ mice (heterozygous for a chain-termination mutation in the $15^{th}$ exon of the APC gene) are regarded as reliable models of spontaneous tumorigenesis, developing multiple intestinal adenomas that clinically mimic those observed in patients with familial adenomatous polyposis [1,2]. Published microarray data has quantified the changes in gene expression accompanying transformation of $APC^{Min/+}$ intestinal epithelium from normal morphology to adenomas and carcinomas [3].

Native catE is an intracellular, non-lysosomal, aspartic protease comprised of two disulfide-linked monomeric subunits of 42 kDa, although several mono- and dimeric proenzyme and glycosylated forms have been reported in expression systems and in vivo [4,5]. The monomeric form can be obtained under mild reducing conditions and is catalytically indistinguishable from the mature dimmer [4]. The tissue distribution of the mammalian enzyme and its transcript are limited and most prevalent in the gastric epithelium [6], although relatively robust expression has also been noted in spleen, thymus, bladder, and erythrocyte membranes [7]. CatE is believed to function as a major component of the proteolytic processing machinery for antigen fragment presentation by then major histocompatibility complex, class II [8]. Pathophysiologically, increased catE levels in human gastric and pancreatic adenocarcinomas have been established [9-11]. However, a detectable increase in tissue or urine catE levels has not been established for the diagnosis or detection of colon cancer.

A non-invasive test, such as a urine test, has not yet been established for colon cancer. A need continues to exist in the medical arts for a reliable marker of colon cancer that may be used to detect and track the pathology of this disease.

SUMMARY

In one aspect of the present invention, a marker for intestinal cancer is provided. In some embodiments, the marker comprises an elevated urine concentration of cathepsin E (catE) or an elevated tissue concentration of cathepsin E transcript (catE), relative to a control catE concentration. In some embodiments, the tissue is a tissue obtained from the intestine.

In another aspect of the present invention, a method for diagnosing and/or providing a routine clinical screen for colon cancer is provided. In some embodiments, the method comprises measuring a cathepsin E concentration in a test urine sample to provide a test cathepsin E concentration, and comparing the test cathepsin E concentration to a control cathepsin E urine concentration, wherein an elevated test cathepsin E urine concentration in the test urine sample is diagnostic of colon cancer. One advantage, among others, of the methods are that they are non-invasive, and are readily implemented as part of a routine clinical screening protocol or panel laboratory testing schedule.

In yet another aspect of the present invention, a method is provided comprising diagnosing and/or screening for colon cancer. In some embodiments, the method comprises measuring cathepsin E concentration in a tissue sample to provide a test cathepsin E tissue concentration, and comparing the test cathepsin E tissue concentration to a control cathepsin E tissue concentration, wherein an elevated test cathepsin E tissue concentration relative to the control cathepsin E tissue concentration is diagnostic of colon cancer.

In a still further aspect of the present invention, a method for assessing tissue dysplasia severity is provided. In some embodiments, the method comprises determining a tissue concentration of cathepsin E, wherein the tissue concentration of cathepsin E correlates with the level of tissue dysplasia severity. In some embodiments of the method, a higher relative concentration of cathepsin E correlates and/or is indicative of a greater degree of tissue dysplasia severity. In particular embodiments, the level of catE is determined by an immunohistochemical technique, wherein areas of tissue dysplasia appear as highly immunostained areas of the tissue specimen.

BRIEF DESCRIPTION OF THE DRAWINGS

The invention will be described in conjunction with the accompanying drawings, in which:

FIG. 4A: Mean urine concentrations (SEM) for 90-old day APCMin/+ (n=33) and wild-type (n=21) mice; FIG. 4B: Mean urine concentrations (SEM) for 60-day old APCMin/+ (n=12) and wild-type (n=13) mice.

DETAILED DESCRIPTION

Figure 1:
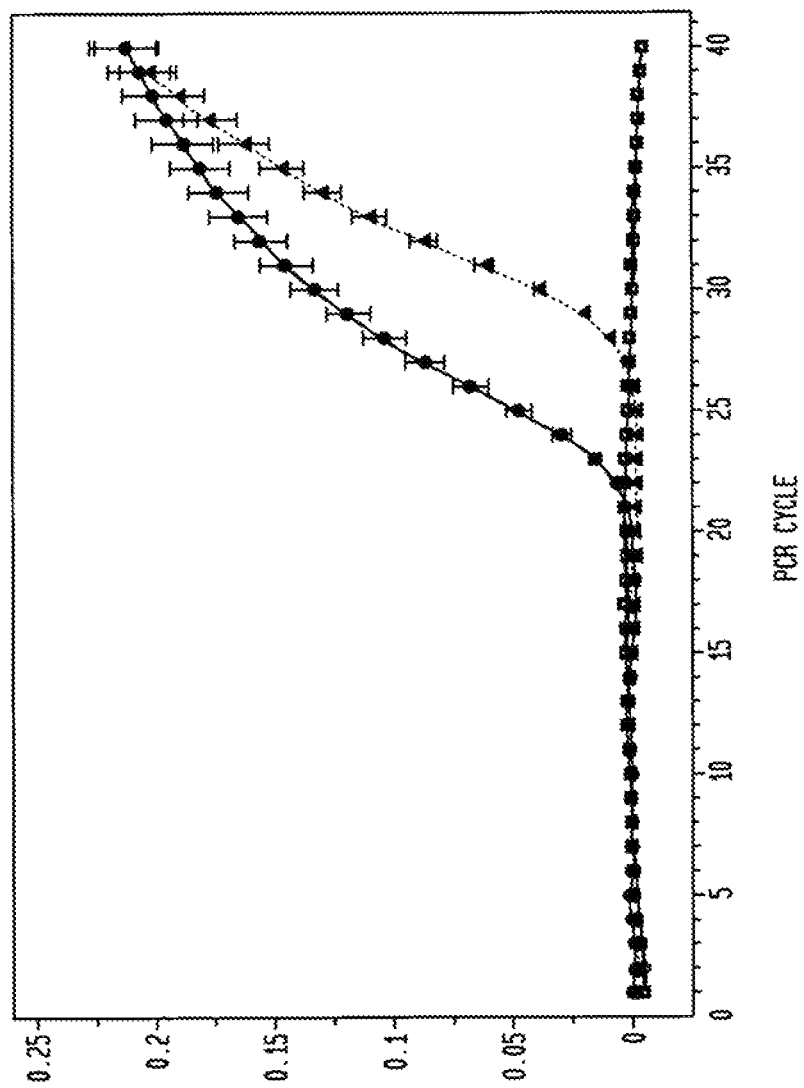
FIG. 1, according to one aspect of the invention, relates to Real-time RT-PCR amplification and detection of catE mRNA. Results represent the average (±SEM) from the total RNA derived from three individual sample collections run in triplicate as described in Example 1, "Materials and Methods." (□) normal intestinal epithelia of $APC^{Min/+}$ mice, 100 ng total RNA (■) normal intestinal epithelia from wild-type mice, 100 ng total RNA; (●) epithelial tissue from $APC^{Min/+}$ adenomas, 100 ng total RNA; (▲) homogenized wild-type spleen, 0.16 ng total RNA.

Aspects of the present invention are generally directed to methods of detecting colon cancer, and more particularly, to a method for detecting colon cancer using a marker such as cathepsin E (catE). Certain embodiments of the present invention, in a general and overall sense, relate to the identification of a correlation between cathepsin E levels, detectable in urine (as a monomeric catE), as well as in tissue (in the form of catE mRNA transcript levels), and the presence of an intestinal form of cancer in an animal, particularly colorectal forms of cancer.

Hence, in one aspect of the present invention, a marker for intestinal cancer is provided. In some embodiments, the marker comprises an elevated urine concentration of cathepsin E (catE) or an elevated tissue concentration of cathepsin E transcript (catE), relative to a control catE concentration. In some embodiments, the tissue is a tissue obtained from the intestine.

In another aspect, a method for diagnosing and/or providing a routine clinical screen for colon cancer is provided. In some embodiments, the method comprises measuring a cathepsin E concentration in a test urine sample to provide a test cathepsin E concentration, and comparing the test cathepsin E concentration to a control cathepsin E urine concentration, wherein an elevated test cathepsin E urine concentration in the test urine sample is diagnostic of colon cancer. One advantage, among others, of the methods are that they are non-invasive, and are readily implemented as part of a routine clinical screening protocol or panel laboratory testing schedule.

In some embodiments, the method provides for the measurement of monomeric forms of cathepsin E in a urine sample using a standard anti-cathepsin E antibody, such as an anti-cathepsin E polyclonal antibody. The increased concentration of catE in the urine of animals having a colon tumor demonstrates an increase in tumor proliferation in these animals, and is reflected in an increase in the renal clearance of catE (monomeric, urinary catE forms) detectable in urine. While not intending to be limited to any particular mechanism of action or theory of operation, the specific increase in the monomeric form of urinary catE observed according to the method may reflect an atypical post-translational processing of the catE gene product in transformed cells, leading to a shift from intracellular localization of catE, to secretion.

By way of example, the test urine sample is a human urine sample. In some embodiments, a test urine sample concentration of cathepsin E that is indicative of colon cancer is 20%, 40%, 50%, 80% or even 100% greater than a control cathepsin E urine concentration. In some embodiments, the concentration of cathepsin E in a test urine sample obtained from an animal having colon cancer or diagnosed to have colon cancer will be elevated 2-fold, 3-fold, or even 5-fold, over the urine concentration of cathepsin E in a control urine sample.

A control cathepsin E concentration may be obtained from a human or other animal known to not have colon cancer. By way of example, such a control cathepsin E urine concentration may be determined using a wild-type mouse or normal human population pool of urine samples.

In some embodiments, the cathepsin E form that is elevated in animals having a form of colon cancer may be further described as a monomeric form of cathepsin E. This monomeric form of cathepsin E may be further defined as having a molecular weight of 46 kDa (mouse). The molecular weigh of the murine antibody for catE is 100 kDaltons.

The cathespin E that may be used as a marker or as any part of the methods described herein may be further described as a native, or "wild-type" form of the monomeric cathepsin E, or a recombinant form of monomeric cathepsin E.

In yet another aspect, a method is provided comprising diagnosing and/or screening for colon cancer. In some embodiments, the method comprises measuring cathepsin E concentration in a tissue sample to provide a test cathepsin E tissue concentration, and comparing the test cathepsin E tissue concentration to a control cathepsin E tissue concentration, wherein an elevated test cathepsin E tissue concentration relative to the control cathepsin E tissue concentration is diagnostic of colon cancer.

In some embodiments, the tissue sample is a human tissue sample, such as an intestinal tissue sample. In some embodiments, the cathepsin E tissue concentration is a measure of the mRNA cathepsin E transcript content of the tissue sample. Hence, in some embodiments, an elevated concentration or amount of cathepsin E mRNA transcript in a test tissue sample (intestinal sample), is diagnostic/indicative of colon cancer in the animal/human from which it was obtained. In other embodiments, the cathepsin E tissue concentration may be determined as a measure of immunohistochemcial staining for catE demonstrated on the tissue sample. Strong, highly specific areas of immunohistochemical staining of a tissue for catE are correlated with areas of very severe dysplastic lesions. The immunohistochemcial staining for catE is therefore also evidence of the existence of colon cancer dysplastic lesions in the animal from whom the tissue was obtained.

In yet another aspect, a method for assessing tissue dysplasia severity is provided. In some embodiments, the method comprises determining a tissue concentration of cathepsin E, wherein the tissue concentration of cathepsin E correlates with the level of tissue dysplasia severity. In some embodiments of the method, a higher relative concentration of cathepsin E correlates and/or is indicative of a greater degree of tissue dysplasia severity. In particular embodiments, the level of catE is determined by an immunohistochemical technique, wherein areas of tissue dysplasia appear as highly immunostained areas of the tissue specimen.

In some embodiments, the method may be further defined as comprising determining a tissue level of cathepsin E by immunostaining the tissue with an anti-cathepsin E antibody to provide an immunostained tissue having a relative intensity level of immunostaining, and correlating the tissue dysplasia severity with the relative intensity level of tissue immunostaining observed. By way of example, a high degree of immunostaining is indicative of a tissue having a severe degree of tissue dysplasia. In some embodiments, the anti-cathepsin E antibody is a polyclonal anti-cathepsin E antibody.

EXAMPLE 1

Materials and Methods

The present example sets forth the various materials and methods that were used in generating the disclosure presented herein.

Mice and Tissue Processing

Mice were maintained in a facility accredited by the Association for Assessment and Accreditation of Laboratory Animal Care (AAALAC), International. Mouse protocols were reviewed and approved by the University of Notre Dame Institutional Animal Care and Use Committee. The APC$^{Min/+}$ colony was generated from C57B16/J APC$^{Min/+}$ mice purchased from Jackson Laboratories (Bar Harbor, Me.). The mice were kept on a standard rodent diet. Animals were sacrificed by CO2 asphyxiation, and their intestines removed, rinsed in phosphate-buffered saline, and incised. Tissues were immediately fixed with 10% formalin, processed, embedded in paraffin, and sectioned (4 μm). Sections were stained with hematoxylin-eosin (H & E).

Laser Capture Microdissection (LCM)

Cryosections (8 μm) from the frozen ilea of 90-day old mice were stained with the HistoGene® LCM Frozen Section Staining Kit (Arcturus, Mountain View, Calif.). Normal epithelial cells from APC and wild-type mice, and epithelial cells from APC adenomas were captured using the Arcturus PixCell IIe LCM system. Each sample necessitated three full CapSure HS caps (Arcturus). Extraction and isolation of the RNA was accomplished using the PicoPure RNA Extraction Kit, Arcturus (Mountain View, Calif.). To obtain sufficient RNA for real-time RT-PCR analysis, two rounds of mRNA amplification was carried out following incorporation of a T7 RNA polymerase promoter sequence into the first cDNA strand.

Real-time RT-PCR

Primers and probes for RT-PCR were designed using Primer Express software (ABI, Foster City, Calif.) and were synthesized by MWG-Biotech (High Point, N.C.). The specificity of each primer set was first tested by RT-PCR, followed by melting curve analysis using an ABI SYBR Green kit with an ABI Prism 7700 Sequence Detection System, and gel electrophoresis of the PCR products. Gene-specific probes (5'-FAM- and 3'-TAMRA-labeled) were then designed to hybridize to the corresponding PCR products. The forward and reverse CatE primers were TCGAGTGTCAATGAAC-CCCTC (SEQ ID No. 1) and GGTGCAGTACACAGAAGG-GAC (SEQ ID No. 2), respectively. The probe used for detection was FAM-TCATCTTTGACACCGGTTCATCCAACC-BHQ1(SEQ ID No. 3).

As an endogenous control, ribosomal protein L19 (RPLI9) expression was monitored in each PCR reaction. The forward and reverse primers for RPLI9 were ATGTATCACAGCCT-GTACCTG (SEQ ID No. 4) and TTCTTGGTCTCCTCCTC-CTTG (SEQ ID No. 5), respectively.

The detection probe was JOE-TTCTTGGTCTCCTC-CTCCTTG-BHQ1 (SEQ ID No. 6).

Each PCR reaction was carried out in triplicate in a total volume of 30 μL containing 0.025 U/μL of ABI AmpliTaq Gold® DNA Polymerase in 1× Buffer A, 0.25 U/μL of Multiscribe reverse transcriptase (ABI, Poster City, Calif.), 0.3 U/μL of Prime RNasin (Eppendorf, Westbury, N.Y.), 4 mM MgCl$_2$, 300 mM each dNTP (Roche, Indianapolis, Ind.), 200 nM probe, 112 nM each primer, and 100 ng total RNA. Thermocycling conditions were as follows: 48° C. for 30 min and 95° C. for 10 min, followed by 40 cycles at 95° C. for 15 s. and 60° C. for 1 min, with fluorescent readings at the end of each cycle. Total RNA (0.16 ng) from spleen tissue was used as a positive control.

Histology and Immunohistochemistry

Abnormal pathologies were classified as gastrointestinal intraepithelial neoplasia (GIN) lesions and adenomas based on recently recommended criteria [2]. For immunohistochemical analysis, sections were cleared with xylene, rehydrated in ethanol/H$_2$O, and treated in 0.01 M citrate buffer (pH 6.0) at 100° C. for 10 min. Residual peroxidase activity was blocked with Peroxo-Block (Zymed, San Francisco, Calif.), followed by overnight incubation in a solution (10 μg/mL) of goat anti-mouse polyclonal antibody to recombinant murine cathepsin E (R & D Systems, Minneapolis, Minn.). Slides were then treated with rabbit anti-goat IgG (DakoCytomation, Carpinteria, Calif.), followed by incubation in goat peroxidase-antiperoxidase (DakoCytomation). Visualization was accomplished using 3-amino-9-ethyl carbazole (AEC) as the chromogen (Vector Laboratories, Burlingame, Calif.). Sections of wild-type mouse stomach were employed as a positive control for catE immunoreactivity.

Western Immuno Blot Analyses

Urine samples from wild-type and APC$^{Min/+}$ mice were collected at 60 and 90 days. If not used immediately, samples were stored at −80° C. (samples have been stored for up to 3 months without any alterations in original catE integrity as analyzed by Western blot). A 10 μL aliquot of each urine sample was combined with 10 μL of SDS-PAGE non-reducing gel loading buffer and incubated for 2 min at 95° C. A 15 μL aliquot of each solution, as well as a sample (160 ng) of murine catE (R & D Systems), was loaded onto precast 4-10% gradient tris-glycine gels (BioWhittaker Molecular Applications, Rockland, Md.) and subjected to electrophoresis at 125 V for 90 min. Protein bands were electroblotted onto PVFD nitrocellulose membranes (Millipore Corporation, Bedford, Mass.). Membranes were incubated with polyclonal goat anti-mouse cathepsin E (see above) and rabbit anti-goat IgG conjugated to alkaline phosphatase (BioRad Laboratories, Inc., Hercules, Calif.). Positive bands were visualized with nitro blue tetrazolium/bromochloroindolyl phosphate. No evidence for the cross reactivity of anti-murine catE with authentic murine cathepsin D (R and D Systems) was discernible at protein loads up to 5 μg.

The molecular weight of Human Cathpsin E: 42,796 Da. This is also expected to be the mouse molecular weight since they were very similar on gel analysis in the present studies.

The human monclonal Cathepsin E antibody show 100% cross reactivity with the mouse Cathepsin E. The human polyclonal Cathepsin E antibody shows 40% cross reactivity with the mouse Cathepsin E.

Data Analyses

Dried blots were scanned using a flatbed scanner. Regions corresponding to protein bands on the resulting images were analyzed for area and mean gray density using NIH Image, a public domain image processing program available from the National Institutes of Health. Total pixels corresponding to the catE-positive bands were normalized to the total pixels corresponding to the 46 kDa band of murine catE standard (which, in turn, constituted ca. 10% of the total catE load). Data was evaluated using the two-tailed, parametric t test. Confidence levels corresponding to $P \leq 0.05$ were considered significant.

EXAMPLE 2

Real-time RT-PCR Detection of catE mRNA Expression in $APC^{Min/+}$ Adenomas

The present example demonstrates the utility of the invention for providing an RNA profiling screening method for diagnosing and/or detecting and monitoring the progression of colon cancer. In this regard, the present example demonstrates that an increase in catE mRNA transcription, and catE expression (monomeric catE) is markedly increased in dysplastic cells, but not in normal (i.e., from non-dysplastic tissue) cells.

To ensure a homogeneous population of cell types for RNA isolation, LCM was employed for the selection of intestinal epithelia corresponding to adenomatous $APC^{Min/+}$, normal $APC^{Min/+}$, and normal wild-type tissue. Total mRNA from wild-type spleen, in which abundant levels of catE transcript have been previously established [7], was employed as an exogenous positive control.

The results of the real-time RT-PCR monitoring are presented in FIG. 1. After 40 PCR cycles, no amplification of catE mRNA was noted in the wild-type normal and $APC^{Min/+}$ normal samples. In contrast, the average threshold cycle for amplification of samples from $APC^{Min/+}$ adenomas was well within the 40 cycle window (ca. cycle 23). An endogenous control, RPL19, was amplified similarly among the displayed RT-PCR run profiles.

EXAMPLE 3

Immunohistochemcal Detection of catE in Intestinal Lesions of $APC^{Min/+}$ Mice The present example demonstrates that dysplastic tissue is immunohistochemically detectable by the presence of specifically staining tissue using an anti-catE antibody, and that the intensity of immunohistochemical staining obtained is correlated to the severity of the dysplastic lesion.

Figure 2:
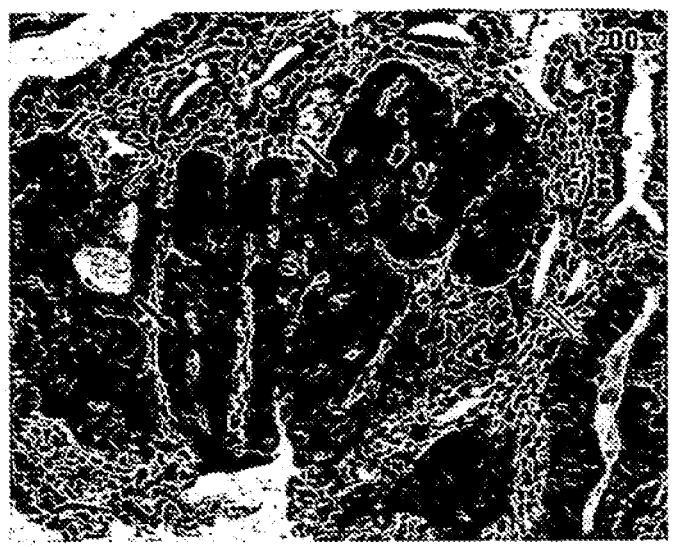
FIG. 2, according to one embodiment of the invention, demonstrates immunohistochemical analysis of intestine from APC$^{Min/+}$ mice using a polyclonal antibody to whole-molecule murine catE. The stained areas correspond to GIN lesions (high disruption of mucosal architecture, crowding, prominent cellular atypia, and elongated nuclei). The regions of high-grade dysplasia are denoted by solid arrows, while the moderate to severe dysplastic areas are labeled with open arrows. Normal glandular cells surrounding the lesions are devoid of stain.

Intestinal sections from a total of 33 90-day old $APC^{Min/+}$ mice were subjected to immunohistochemical analyses with a commercially available polyclonal antibody to catE. Examined sections manifested gastrointestinal intraepithelial neoplasia (GIN) lesions and adenomas; no adenocarcinomas were observed. A representational section of an $APC^{Min/+}$ mouse intestine (FIG. 2) shows catE staining in all regions of the epithelia manifesting mild to severe dysplasia. Normal-appearing areas of the intestine are devoid of detectable staining, as was also observed for sections from wild-type mice. A direct relationship is shown between the severity of the lesions and the intensity of the immunostaining. For instance, the areas presenting high-grade dysplasia are significantly darker than the regions of moderate to severe dysplasia.

EXAMPLE 4

Detection of Increased catE Levels in the Urine of APC Min/+ Mice

The present example demonstrates the utility of the invention for providing a urine test for colon cancer by measuring catE (monomeric forms) levels in the urine sample.

Figure 3:
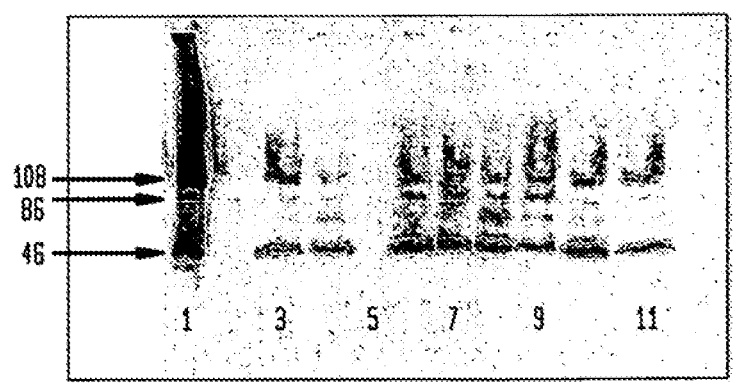
FIG. 3, according to one embodiment of the invention, demonstrates the detection of urinary catE by Western immunoblot anaylsis following SDS-PAGE of urine samples from 90-day old wild-type (lanes 3 and 4) and APCMin/+ mice (lanes 6-11). Membranes were developed with the same polyclonal antibody to catE employed in the immunohistochemical studies. Recombinant murine catE was loaded in lane 1. The indicated molecular weights (kDa) of the various forms of catE were previously determined from separate SDS-PAGE analysis of the recombinant protein run in tandem with ProSieve protein markers (Cambrex, East Rutherford, N.J.).
Figure 4A:
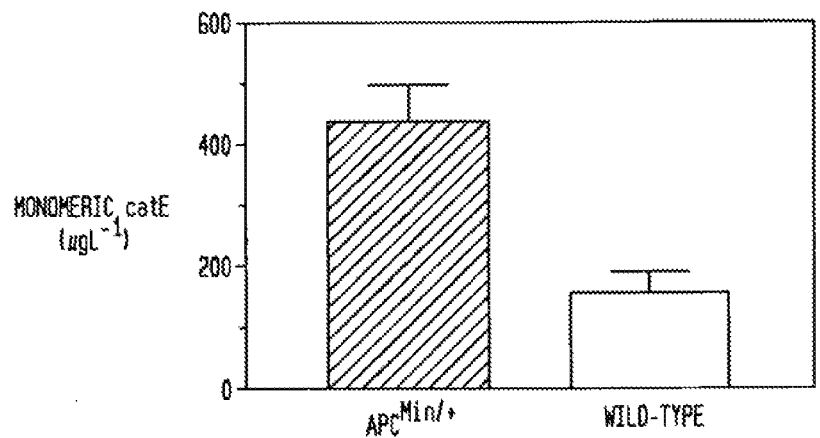
FIGS. 4A-4B, according to one embodiment of the invention, presents the results of NIG Image analysis of the 46 kDa anti-catE positive protein bands from Western blots of APC-Min/+ and wild-type mouse urine.
Figure 4B:
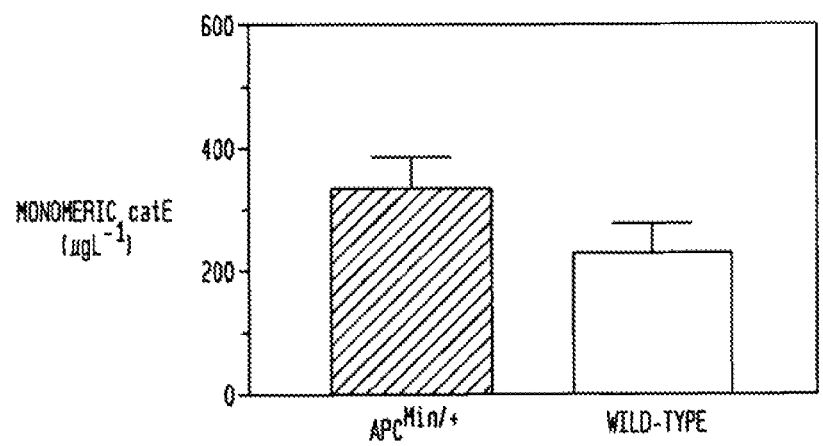

Using Western blot analysis, bands corresponding to the dimeric (108, 86 kDa) and monomeric (46 kDa) forms of catE were observed in the urine of both wild-type and $APC^{Min/+}$ 90-day old mice. As evident in the representative blot in FIG. 3, qualitative inspection of these blots indicated a marked increase in the intensity of the 46 kDa band in the $APC^{Min/+}$ urine specimens, compared to samples from wild-type animals. Quantification of band intensities using NIH Image analysis software revealed a statistically significant (p=0.0012) increase in the amount of monomeric catE present in $APC^{Min/+}$ (n=33) versus wild-type (n=21) urine (FIG. 4A).

Based on the amount of monomeric catE present on each gel as an internal standard (15 ng), the mean concentration of monomeric catE in the urine of $APC^{Min/+}$ mice (±SD) was 436±354 µL$^{-1}$, while wild-type urine contained 158±146 µg L$^{-1}$. No significant differences in monomeric catE concentrations were observed between females and males in either the wild-type or $APC^{Min/+}$ group. Mean monomeric catE urinary concentrations for wild-type females and males were 148±70 µL$^{-1}$ (n=15) and 192±264 µL$^{-1}$ (n=6), respectively (p=0.519). For the $APC^{Min/+}$ mice, values of 408±370 µg L$^{-1}$ (n=21) and 484±332 µL$^{-1}$ (n=12) were obtained for females and males, respectively (p=0.560). A similar analysis was conducted on 60-day old mice (FIG. 3B). For this age group, the concentration of monomeric catE was 337±166 µg L$^{-1}$ and 230±177 µg L$^{-1}$ for $APC^{Min/+}$ mice (n=12), and wild-type animals (n=3), respectively (p=0.137).

EXAMPLE 5

CatE as a Marker of Colon Cancer in Humans

The present example demonstrates the utility of the present invention for use in the detection, quantitation, and pathology of colon cancer in humans. The present example also demonstrates that increased levels of catE are also present in human colon cancers.

Patient Specimens

In collaboration with the Northern Indiana Cancer Research Consortium, normal and colonic tumor tissue specimens were obtained from patients who underwent elective surgical resections following diagnosis of colon cancer. Samples were processed as described herein at Example 1.

Patient samples were treated with a solution of goat anti-human polyclonal antibody to recombinant human cathepsin E (R & D Systems). Slides were then treated with rabbit anti-goat IgG (DakoCytomation, Carpinteria, Calif.), followed by incubation in goat peroxidase-antiperoxidase (DakoCytomation). Visualization was accomplished using 3-amino-9-ethyl carbazole (AEC) as the chromogen (Vector Laboratories, Burlingame, Calif.). Sections of wild-type mouse stomach were employed as a positive control for catE immunoreactivity.

Immunohistochemical Detection of catE in Human Colonic Tumors

Figure 5:
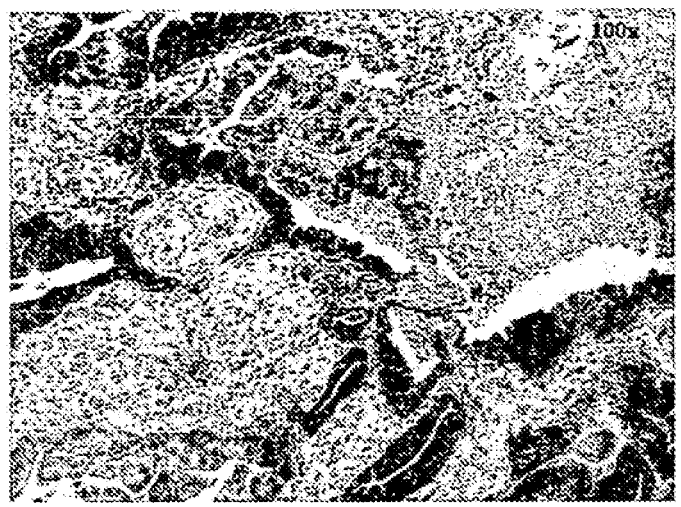
FIG. 5, according to one embodiment of the invention, presents an immunochemical analysis of a section of submucosa from an excised human colonic tumor (invasive malignant glandular neoplasma). Staining was carried out with a polyclonal antibody to recombinant human catE. Stained areas are consistent with marked dysplasia. Areas of normal morphology do not exhibit appreciable staining.

To determine whether human intestinal cancers display increased catE levels that parallel those observed with APC$^{Min/+}$ mice, tumor specimens excised from patients diagnosed with colorectal cancer were examined. Eight of the thirteen individual patient specimens probed for immunoreactivity to anti-catE were moderately to strongly catE-positive. A representative section is shown in FIG. 5. Stained areas present pathologic features similar to those seen in the catE-positive APC$^{Min/+}$ mice sections, including abnormal mucosal architecture, crowding, prominent cellular atypia, and elongated nuclei.

A larger question surrounding the apparent increase in catE levels in APC$^{Min/+}$ mice concerns the relevance of these findings with respect to the human disease. Immunohistochemical evaluation of tumor sections obtained from colon cancer patients reveals moderate to strong anti-catE reactivity in the majority (eight of thirteen) of individual specimens. The level of catE staining observed in the present studies is more robust than previously described for human neoplastic colorectal tissue [13]. While not intending to be limited to any particular theory or mechanism of action, it is noted here that a much shorter primary antibody incubation period was described in the prior study. Additionally, the anti-catE used in the present studies was elicited with recombinant human catE while, in the aforementioned work, the antigen was a peptide corresponding to a segment of the C-terminal domain of catE.

The evident similarities in catE distribution in APC$^{Min/+}$ mouse and human colorectal lesions establishes a predicate for urinary catE levels in preoperative colon cancer patients being different (i.e., higher urinary catE) from those of healthy human subjects in a manner that parallels catE abundance in APC$^{Min/+}$ versus wild-type mouse urine.

The present immunohistochemical analyses of tumor sections from colon cancer patients establishes reliable predicate for catE as a biological marker in the diagnosis and prognosis of the human disease.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for diagnosing colon cancer comprising:
obtaining a tissue sample from a patient to provide a test tissue sample;
measuring cathepsin E concentration in the test tissue sample to provide a test tissue cathepsin E concentration;
comparing said test tissue cathepsin E concentration to a control cathepsin E tissue concentration; and
diagnosing colon cancer in the patient where the test tissue cathepsin E concentration is higher than the control cathepsin E tissue concentration obtained from a patient without colon cancer.

2. The method of claim 1 wherein the tissue sample is an intestinal tissue sample.

3. The method of claim 1 wherein the tissue sample is a human intestinal tissue sample.

4. The method of claim 1 wherein the tissue cathepsin E concentration is determined by immunostaining the tissue with an anti-cathepsin E antibody, wherein the relative intensity level of immunostaining provides a measure of the cathepsin E in the tissue.

5. A method for detecting tissue dysplasia of colon cancer in a patient tissue comprising:
obtaining a patient intestinal tissue sample to provide a test tissue sample;
measuring a test tissue concentration of cathepsin E from the patient intestinal tissue and a control tissue concentration of cathepsin E from a control intestinal tissue sample obtained from a patient without colorectal tissue dysplasia using an immunostaining method;
comparing the cathepsin E concentration of the test tissue to the control tissue concentration to identify a patient having a higher cathepsin E than the control tissue; and
detecting a patient having tissue dysplasia of colon cancer where the test tissue has a higher cathepsin E concentration than the control tissue cathepsin E concentration or detecting a patient with an absence of dysplasia where the test tissue has a cathepsin E concentration that is comparable to the control tissue cathepsin E concentration.

6. The method of claim 5 wherein the intestinal tissue is human intestinal tissue.

7. The method of claim 6 wherein measuring a tissue concentration of cathepsin E comprises immunostaining the tissue with an anti-cathepsin E antibody.

8. The method of claim 7 wherein the anti-cathepsin E antibody is a monoclonal antibody.

9. The method of claim 7 wherein the anti-cathepsin E antibody is a polyclonal antibody.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgagtgtca atgaacccct c                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtgcagtac acagaaggga c                                               21

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tcatctttga caccggttca tccaacc                                         27

<210> SEQ ID NO 4
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 4
atgtatcaca gcctgtacct g                                                   21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcttggtct cctcctcctt g                                                   21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ttcttggtct cctcctcctt g                                                   21
```